United States Patent [19]

Janssens

[11] 4,232,107
[45] Nov. 4, 1980

[54] PHOTOGRAPHIC MATERIAL SUITED FOR USE IN DIFFUSION TRANSFER PHOTOGRAPHY AND METHOD OF DIFFUSION TRANSFER PHOTOGRAPHY USING SUCH MATERIAL

[75] Inventor: Wilhelmus Janssens, Aarschot, Belgium

[73] Assignee: AGFA-GEVAERT N.V., Mortsel, Belgium

[21] Appl. No.: 20,651

[22] Filed: Mar. 15, 1979

[30] Foreign Application Priority Data

Mar. 22, 1978 [GB] United Kingdom ............... 11445/78

[51] Int. Cl.$^3$ .................. G03C 1/40; G03C 5/54; G03C 1/10; G03C 1/48
[52] U.S. Cl. ........................ 430/223; 430/212; 430/217; 430/218; 430/227; 430/236; 430/239; 430/240; 430/242; 430/244; 430/543; 430/559; 430/564; 430/566; 430/598; 430/599; 430/621; 430/965
[58] Field of Search ............. 96/29 R, 29 D, 76 R, 96/77, 95, 99, 100, 109, 96, 107, 111, 101; 430/223, 240, 242, 239, 236, 559, 566, 543, 598, 599, 621, 965, 564, 212, 227, 244, 218, 217

[56] References Cited

U.S. PATENT DOCUMENTS

| | | | |
|---|---|---|---|
| 3,698,898 | 10/1972 | Grasshoff et al. ............... | 96/77 |
| 3,728,113 | 4/1973 | Becker et al. .................. | 96/77 |
| 3,980,479 | 9/1976 | Fields et al. ................... | 96/77 |
| 4,139,379 | 2/1979 | Chasman et al. ............... | 96/77 |

FOREIGN PATENT DOCUMENTS 861241 5/1978 Belgium .

Primary Examiner—Richard C. Schilling
Attorney, Agent, or Firm—A. W. Breiner

[57] ABSTRACT

Said material contains a quinone-type compound which corresponds to one of the formulae (A) or (B) and which is capable in reduced state and under alkaline conditions of releasing a photographically useful group e.g. a dye:

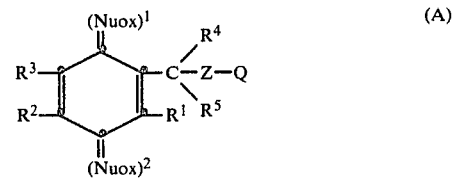

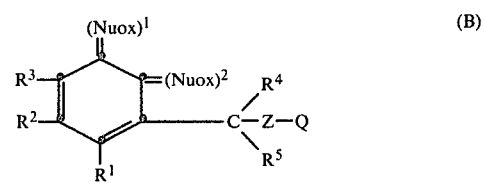

wherein:
each of $(Nuox)^1$ and $(Nuox)^2$ represents an oxidized nucleophilic group,
Z represents a bivalent atomic group which is electronegative,
Q together with the Z group represents a releasable photographically useful group,
each of $R^1$, $R^2$ and $R^3$ is hydrogen, halogen, alkyl, alkoxy, or an acylamino group or $R^1$ and $R^2$ in adjacent positions on the ring form a ring fused with the remainder of the molecule, or $R^2$ and $R^3$ together are fused with the remainder of the molecule.
each of $R^4$ and $R^5$ represents hydrogen or a hydrocarbon group.

At least one of the substituents $R^1$, $R^2$, $R^3$, $R^4$ or $R^5$ is a ballasting group X.

12 Claims, No Drawings

PHOTOGRAPHIC MATERIAL SUITED FOR USE IN DIFFUSION TRANSFER PHOTOGRAPHY AND METHOD OF DIFFUSION TRANSFER PHOTOGRAPHY USING SUCH MATERIAL

The present invention relates to a photographic material suited for use in diffusion transfer photography and to a method of diffusion transfer photography using such material.

Photographic diffusion transfer processes have been known for several years and are summarized e.g. in "Imaging Systems" by Kurt I. Jacobson and Ralph E. Jacobson (1977), The Focal Press.

Photographic image-transfer processes are based on image formation in a photosensitive image-recording layer and diffusion in an image-wise pattern of at least one substance out of said layer to form an image in an adjacent image-receiving layer and/or to leave an image-wise distributed transferred substance in said image-receiving layer.

In the generally known black-and-white DTR-process (diffusion transfer reversal process) a silver salt complex is image-wise transferred from an image-wise exposed silver halide emulsion layer to an image-receiving material wherein, with the aid of a developing agent and promoted by development nuclei, the silver salt complexes are reduced to silver.

In diffusion transfer colour processes an image-dye-providing substance is associated with a silver halide emulsion. An image-dye-providing substance, which provides a positive transferred image in an image-receiving material dependent on development of a conventional negative silver halide emulsion, is referred to as positive-working. Likewise, an image-dye-providing material, which provides a negative transferred image in an image-receiving layer dependent on development of a conventional negative silver halide emulsion, is referred to as negative-working.

Dye-diffusion systems operating with photosensitive silver halide can be carried out in a number of ways, but tney are all based on the same principle, viz. the alteration in the mobility of a dye or dye-forming structural part of a compound controlled by the image-wise reduction of the photosensitive silver halide.

The image-forming substances used in colour image-transfer processes can therefore be defined as being initially mobile or initially immobile substances. These terms are generally understood to mean that the image-forming substance is either diffusible or non-diffusible in the photographic element when the latter is permeated with the processing liquid used to carry out the diffusion transfer process. The immobile substances are generally ballasted to provide sufficient immobility in the photographic element when it is imbibed with the processing solution so that these substances will not diffuse substantially from their initial location. A particular class of immobile substances contains compounds that undergo a cleavage or displacement reaction to release a diffusible moiety in an image-wise pattern during the alkaline processing of image-wise exposed silver halide. The formed mobile compounds will diffuse in the photographic element until they are rendered insoluble or immobile in an image-wise pattern in a receptor material.

An important class of initially immobile image-dye-providing compounds have the property of releasing or producing a diffusible dye in proportion to the development of the associated silver halide emulsion by a displacement coupling reaction with an oxidized developing agent for photo-exposed silver halide.

Said initially immobile image-dye-providing compounds are normally called diffusible dye-releasing compounds (DDR-compounds). The displacement coupling reaction requiring two reagents, the DDR-compound and developing agent, e.g. an aromatic primary amino colour developer or catechol, can proceed in two different ways by using different types of DDR-compound, which are called a type (A) and a type (B) compound herein. A type (A) compound is a compound e.g. coupler with solubilizing group and which through a splittable link is bound to a ballast group. A type (B) compound is a compound e.g. coupler with ballast group and which through a splittable link is bound to a dye with solubilizing group. Compounds of said both types and a survey of suitable splittable linkages and solubilizing groups are described in the U.K. Pat. No. 904,364, filed Sept. 11, 1958 by Kodak Limited. In connection with the type (A) compounds further reference is made, e.g., to the U.S. Pat. No. 3,227,550 of Keith E. Whitmore and Paul M. Mader, issued Jan. 4, 1966, 3,628,952 of Walter Puschel, Justus Danhauser, Karlheinz Kabitzke, Paul Marx, Arnfried Melzer, Karl-Wilhelm Schranz and Hans Vetter, issued Dec. 21, 1971 and 3,844,785 of Walter Puschel, Hans Vetter and Heinrich Odenwalder, issued Oct. 29, 1974, and the published German Patent Applications (DT-OS) Nos. 2,317,134 filed Apr. 5, 1973 by AgfaGevaert A.G. and 2,415,125 filed Mar. 28, 1974 by Konishiroku.

Type (B) compounds defined as initially immobile compounds, which release a diffusible image-providing dye in an amount that is inversely proportional to the amount of developed associated silver halide, are described in the published German Patent Application (DT-OS) No. 2,402,900 filed Jan. 22, 1974 by Eastman Kodak Company.

In its broadest aspect the latter German Patent Application relates to a photographic element comprising a support having thereon at least one alkali-permeable layer containing a photosensitive substance such as silver halide and at least one alkali-permeable layer containing a non-diffusible compound having a photographically useful group wherein said compound is capable of releasing said photographically useful group under alkaline conditions, and is also capable of reaction with an oxidized developing agent for said photosensitive substance, wherein the reaction product has a substantially lower rate of release of the photographically useful group under said alkaline conditions.

In said German Patent Application compounds capable of releasing a photographically useful substance are described, which compounds are initially immobile in an alkali-permeable colloid medium and contain an electrophilic cleavage group linking a photographically useful moiety to a ballast moiety and contain also a nucleophilic group, which is capable of (1) interacting with said electrophilic cleavage group to release a diffusible photographically useful substance under alkaline conditions and (2) of reacting with an oxidized silver halide developer before any substantial release of said photographically useful substance occurs to lower substantially the rate of release of said photographically useful group under alkaline conditions. Very suitable compounds of that type contain as an electrophilic cleavage group a carbamic acid derivative as described in U.S. Pat. No. 3,980,479 of Donald Lee Fields, Richard Paul Henzel, Philip Thiam Shin Lau and Richard Allan Chasman issued Sept. 14, 1976.

The reaction mechanism put forward in the latter patent specification and illustrated by simplified formulae is as follows:

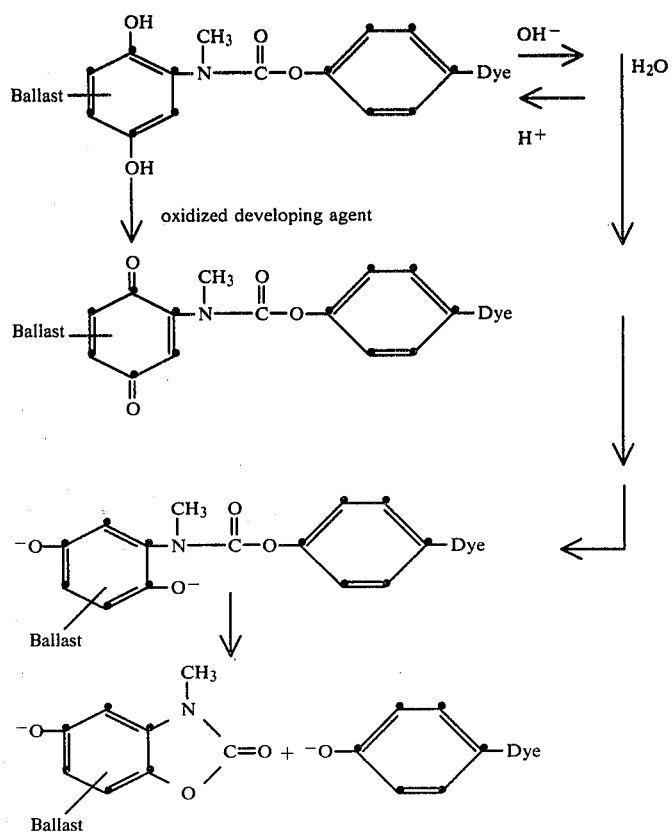

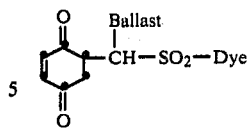

The photographically useful moiety such as a dye is released where the nucleophilic group, such as the hydroxyl group of the hydroquinone, can attack the carbamate ester linkage. However, when the nucleophilic group is oxidized, such as when the hydroquinone is oxidized to form a quinone, nucleophilic displacement is prevented.

Other compounds capable of releasing a photographically useful substance e.g. dye under alkaline conditions are described in the Belgian Pat. No. 861,241 filed Nov. 28, 1977 by Agfa-Gevaert N.V.

The reaction mechanism followed in the release of said substance by said compounds is illustrated by simplified general formulae as follows:

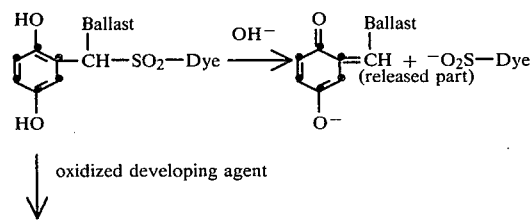

The advantage of the use of such type of compounds (as described in the foregoing two patents) lies in the possibility of producing positive colour images in combination with negative-working silver halide emulsions whose composition is less sophisticated than that of positive-working silver halide emulsions and that can be manufactured with a much higher light-sensitivity than positive-working silver halide emulsions can obtain. Moreover, negative-working silver halide emulsions develop much faster than positive-working silver halide emulsions, which is an important advantage especially on applying in-camera processing.

In accordance with the present invention a photographic silver halide material comprising a support carrying at least one unexposed alkali-permeable silver halide hydrophilic colloid emulsion layer is provided which contains in operative contact therewith or therein a quinone type compound, which compound is initially immobile in an alkali-permeable colloid medium and wherefrom through the reducing action of a silver halide developing agent and alkalinity a photographically useful substance, e.g. a dye, a dye precursor, a colour coupler, a fog-inhibiting compound, a development-retarding compound or another species active in photographic imaging, can be split off in diffusible state said quinone type compound corresponding to one of the general formulae (A) and (B):

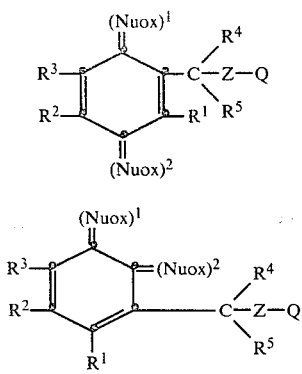

(A)

(B)

wherein:
each of (Nuox)¹ and (Nuox)² (same or different) represents an oxidized nucleophilic group such as a O= group or NH= group,
Z represents a bivalent atomic group, which is electronegative with respect to the carbon atom carrying $R^4$ and $R^5$, e.g. a sulphonyl group,
Q together with the Z group represents a releasable photographically useful group, e.g. a diffusible dye group,
each of $R^1$, $R^2$ and $R^3$ is a mono-atomic group e.g. hydrogen, a halogen atom, or a polyatomic group, e.g. an alkyl group, an alkoxy group, an acylamino group wherein the acyl group is derived from aliphatic or aromatic carboxylic or sulphonic acids, or $R^1$ and $R^2$ together when in adjacent positions on the ring form a ring fused with the remainder of the molecule, e.g. a benzene ring, or $R^2$ and $R^3$ together form a ring fused with the remainder of the molecule, e.g. a benzene ring, and
each of $R^4$ and $R^5$ (same or different) represents hydrogen or a hydrocarbon group including a substituted hydrocarbon group, e.g. an alkyl group.

In at least one of the substituents $R^1$, $R^2$, $R^3$, $R^4$ or $R^5$ a ballasting group X e.g. alkyl group of sufficient size is present to render said compound immobile in an alkali-permeable layer of the photographic material.

The term "non-diffusing" used herein has the meaning commonly applied to the term in photography and denotes materials that in any practical application do not migrate or wander through organic colloid layers in an alkaline medium, such as gelatin, in the photographic elements of the invention. The same meaning is to be attached to the term "immobile".

The term "diffusible" as applied to the materials of this invention has the converse meaning and denotes materials having the property of diffusing effectively through the colloid layers of the photographic elements in an alkaline medium. "Mobile" has the same meaning.

By "operative contact" is meant that in the present invention for producing diffusion transfer of an image-wise released photographically useful substance on applying an alkaline processing liquid in the presence of a photographic silver halide developing agent, said quinone-type compound can come into chemically reactive contact with the developing agent in an amount that is controlled by the image-wise developable silver halide of the image-wise photo-exposed silver halide emulsion layer.

The above quinone type compounds may be sufficiently resistant to diffusion even when the above mentioned substituents do not contain long alkyl residues, because the molecule of the dye residue may itself be sufficiently large. In other cases, the compounds may be rendered sufficiently resistant to diffusion by providing them with sufficiently large residues.

Residues which confer diffusion resistance are residues which allow the compounds according to the invention to be incorporated in a diffusion resistant form in the hydrophilic colloids normally used in photographic materials. Organic residues which generally carry straight or branched chain aliphatic groups and which may also carry isocyclic or heterocyclic or aromatic groups generally having from 8 to 20 carbon atoms are preferably used for this purpose. These residues are attached to the remainder of the molecule either directly or indirectly, e.g. through one of the following groups: —NHCO—; —NHSO₂—; —NR—, in which R represents hydrogen or alkyl; —O—; —S—; or —SO₂—. The residue which confers diffusion resistance may in addition carry groups which confer solubility in water, e.g. sulpho groups or carboxyl groups, and these may also be present in an anionic form. Since the diffusion properties depend on the molecular size of the compound as a whole, it is sufficient in some cases, for example when the molecule as a whole is large enough, to use shorter chain groups as "groups which confer diffusion resistance".

Compounds within the scope of the general formulae (A) and (B) but wherein (Nuox)¹ and (Nuox)² are reduced to nucleophilic groups (Nu)¹ and (Nu)² such as —OH and —NH₂ and their synthesis are described e.g. in the Belgian Patent No. 861,241 filed Nov. 28, 1977 by Agfa-Gevaert N.V., claiming priority of German Patent application P No. 26 54 213 filed Nov. 30, 1976 by Agfa-Gevaert A.G.

The preparation of compounds according to the above general formulae (A) and (B) can proceed by treating the corresponding reduced compounds, i.e. compounds with the nucleophilic groups (Nu) in unoxidized state, with an oxidizing agent such as p-benzoquinone in excess in a solvent, e.g. refluxing ethanol.

Other oxidizing agents suited for use in the synthesis of compounds of general formula (A) or (B) are:
methyl-1,4-benzoquinone
2,5-dimethyl-1,4-benzoquinone
octyl-1,4-benzoquinone
dodecyl-1,4-benzoquinone
2,3,5-trimethyl-1,4-benzoquinone
1,4-naphthoquinone
2-methyl-1,4-naphthoquinone
2-octyl-1,4-naphthoquinone
2-dodecyl-1,4-naphthoquinone
5,8-methano-1,4-naphthoquinone
9,10-o-benzeno-1,4-anthraquinone
2,6-dimethyl-1,4-benzoquinone
2,6-dichloro-1,4-benzoquinone.

The quinone type compounds used in a photographic material of the present invention have as such no reducing properties and must be reduced image-wise to obtain the capability of releasing image-wise a photographically useful substance in alkaline conditions. Such brings about the advantage of a considerably less fog production on storage and development compared with the use of photographic materials initially containing the compounds in reduced form as described in the prior art e.g. U.S. Pat. No. 3,980,479, already mentioned hereinbefore.

A photographic material according to the present invention comprises in its simplest form a support carrying at least one unexposed alkali-permeable silver halide hydrophilic colloid emulsion layer which contains in operative contact therewith or therein a said quinone-type compound that is immobile in an alkali-permeable colloid medium and that contains a photographically useful group and a ballast group, wherein said compound is capable of being reduced by a silver halide developing agent at a rate slower than that of imagewise developable silver halide in the photographic material and in reduced state is capable of releasing said photographically useful group under alkaline conditions.

The quinone-type compounds for use according to the invention are incorporated in the coating liquid for the layers of a photographic material by one of the usual methods. The quantity of such compound used per liter of coating liquid varies within relatively wide limits e.g. dependent on the photographically useful group that is to be split off and the most suitable concentration can be found with the aid of simple tests. For example, from 5 to 80 g, preferably from 20 to 40 g, of quinone-type compound may be used per liter of coating liquid. The incorporation into the coating liquid e.g. of the silver halide emulsion may proceed by addition of sharp edged sand or by using ultrasound.

According to another method, it may be desired to incorporate the quinone-type compounds in the layer in the form of so-called micro-capsules together with silver halide and optionally also developer substances. In that case, two or more differently sensitized light-sensitive silver halide emulsions and the appropriate diffusion resistant compounds may be combined in a single layer in the form of so-called mixed grain emulsions, for example as described in U.S. Pat. No. 2,698,794 of Leopold Godowsky, issued Jan. 4, 1955. Methods of incorporation in which a quinone-type compound is incorporated into a hydrophilic binder from an alkaline aqueous solution may be applied too since there is no danger of premature hydrolysis of the compound in the quinone form.

The present photographic material can contain (a) negative-working silver halide emulsion layer(s) or (a) positive-working emulsion layer(s) and is capable of providing with negative-working silver halide emulsion layer(s) direct positive colour images by using compounds that in reduced state and under alkaline conditions are capable of releasing a dye, a dye precursor or a colour coupler.

In a particular embodiment said quinone-type compound is present in a hydrophilic colloid layer adjacent to a silver halide emulsion layer, this adjacent layer being preferably situated behind, viewed in the direction of incident light during exposure, the silver halide emulsion layer.

In an embodiment for producing multicolour images this invention relates to photographic materials that comprise a support carrying (1) a red-sensitive silver halide emulsion layer having operatively associated therewith a said quinone-type compound that is initially immobile in an alkali-permeable colloid medium and wherefrom through the reducing action of a silver halide developing agent the alkalinity a cyan dye is split off in diffusible state, (2) a green-sensitive silver halide emulsion layer having operatively associated therewith said compound of (1) with the difference that a magenta dye is split off in diffusible state, and (3) a blue-sensitive silver halide emulsion layer having operatively associated therewith said compound of (1) with the difference that a yellow dye is split off in diffusible state.

The image dye-providing moiety may be a preformed dye or a shifted dye. Dye materials of this type are well-known in the art and include azo dyes, azomethine (imine) dyes, anthraquinone dyes, alizarine dyes, merocyanine dyes, quinoline dyes, cyanine dyes and the like. The shifted dyes include those compounds whose light-absorption characteristics are shifted hypsochromically or bathochromically when subjected to a different environment such as a change in pH, a reaction with a material to form a complex, a tautomerization, reactions to change the pKa of the compound, a removal of a group such as a hydrolyzable acyl group connected to an atom of the chromophore as mentioned in Weyerts, U.S. Pat. No. 3,260,597 of Stanley R. Scales and Allen E. Wisler, issued July 12, 1966, and the like. In certain embodiments, the shifted dyes are highly preferred, especially those containing a hydrolyzable group on an atom affecting the chromophore resonance structure, since the compounds can be incorporated directly in a silver halide emulsion layer or even on the exposure side thereof without substantial reduction in the light that is effective in the exposure of the silver halide. After exposure, the dye can be shifted to the appropriate colour such as, e.g., by hydrolytic removal of an acyl group to provide the respective image dye.

In another embodiment the compounds of this invention contain an image dye-providing moiety, which is an image-dye precursor. The term "image-dye precursor" is understood to refer to those compounds that undergo reactions encountered in a photographic imaging system to produce an image dye such as colour couplers, oxichromic compounds, and the like.

When colour couplers are used, they can be released in areas where no development occurs and can diffuse to an adjacent layer where they can be made to react with an oxidized colour developer such as an oxidized primary aromatic amine to form the image dye. Generally, the colour coupler and the colour developer are chosen so that the reaction product is immobile. Typical useful colour couplers include the pyrazolone couplers, pyrazolotriazole couplers, open-chain ketomethylene couplers, phenolic couplers and the like. Further reference to the description of appropriate couplers is found in U.S. Pat. No. 3,620,747 of John C. Marchant and Robert F. Motter, issued Nov. 16, 1971, which is incorporated herein by reference.

The compounds containing oxichromic moieties can be advantageously used in a photographic system since they are generally colourless materials due to the absence of an image-dye chromophore. Thus, they can be used directly in the photographic emulsion or on the exposure side thereof without competitive absorption. Compounds of this type are those compounds that undergo chromogenic oxidation to form the respective image dye. The oxidation can be carried out by aerial oxidation, incorporation of oxidants into the photographic element or film unit, or use of an oxidant during processing. Compounds of this type have been referred to in the art as leuco compounds, i.e., compounds that have no colour. Typical useful oxichromic compounds include leuco indoanilines, leuco indophenols, leuco anthraquinones and the like.

The compounds described herein have particular application in a diffusion transfer process where it is desired to have a dye entity transferred to an adjacent layer or a receiving element. However, in certain embodiments this invention relates to the release of an image-wise distribution of a diffusible photographically useful compound, which is a photographic reagent. Typical useful photographic reagents are known in the art, such as in U.S. Pat. Nos. 3,227,551 of Charles R. Barr, John Williams and Keith Whitmore, issued Jan. 4, 1966; 3,364,022 of Charles R. Barr, issued Jan. 16, 1968; 3,379,529 of Ralph Frederik Porter, Judith A. Schwan and John W. Gates, issued Apr. 23, 1968 and 3,698,898 of J. Michael Grasshoff and Lloyd D. Taylor, issued Oct. 17, 1972, e.g. a silver-complexing agent, a silver halide solvent, a fixing agent, a toner, a hardener, a fogging agent, a coupler, a sensitizer, a desensitizer, a developer or an oxidizing agent.

The photographically useful group can likewise be a silver halide development inhibitor including triazoles and tetrazoles such as a 5-mercapto-1-phenyltetrazole, a 5-methylbenzotriazole, a 4,5-dichlorobenzotriazole and the like, and it can also be an antifoggant including azaindenes such as a tetrazaindene and the like. The compounds that contain releasable silver halide development inhibitors or antifoggants can generally be used in the photographic elements in association with silver halide layers wherein said compound can be incorporated in amounts such as 11 to 1080 mg/sq.m dissolved in a coupler solvent such as diethyl lauramide. When these compounds are incorporated in photographic elements in association with negative silver halide emulsions, a positive image-wise distribution of inhibitor or antifoggant will be produced upon development. Thus, silver development is inhibited or restrained in the low-exposure toe as seen on the H and D curve, but not in the more fully exposed shoulder as also appears from that curve. Development inhibition of the unexposed areas is achieved thereby selectively. When the silver halide emulsions also have dye releasers in accordance with this invention associated therewith, the overall effect of the inhibitor or anti-foggant is to release more dye in the unexposed regions, improving maximum image-dye density in the image-receiving layer without increasing the amount of dye released in the exposed regions.

The photographically useful group can also be a silver halide development accelerator such as a benzyl alcohol, a benzyl α-picolinium bromide and the like, a foggant including hydrazines and hydrazines such as an acetylphenylhydrazine and the like, or an auxiliary developer such as a hydroquinone, a 1-phenyl-3-pyrazolidinone, ascorbic acid and the like. When these compounds are used in photographic elements in association with silver halide emulsions, which also have associated therewith image dye-providing materials in accordance with this invention, the released-dye density of all dyes in the unexposed regions would be somewhat reduced by fog development. If, however, one layer was unexposed while the other two were given an image-wise exposure, the amount of foggant or development accelerator reaching the unexposed layer from the other two layers would be less where those layers were exposed. Hence, the $D_{max}$ of the unexposed layer would increase in accordance with the exposure of the other two layers. This greatly enhances the saturation of single colours in a photograph.

In a specific embodiment in accordance with this invention a photographic material being a film unit is provided that is adapted to be processed by passing said unit between a pair of juxtaposed pressure-applying members, such as would be found in a camera designed for in-camera processing. The unit comprises (1) a photosensitive element, which contains a silver halide emulsion layer having associated therewith a said quinone-type compound that is initially immobile in an alkali-permeable colloid medium and wherefrom through the reducing action of a silver halide developing agent and alkalinity a dye is split off in diffusible state, (2) an image dye-receiving layer, (3) means for discharging an alkaline processing composition within the film unit such as a rupturable container, which is adapted to be positioned during processing of the film so that a compressive force applied to the container by the pressure-applying members will effect a discharge of the container's contents within the film, and (4) a silver halide developing agent, which is soluble in the alkaline processing composition located within said film unit.

The photographic material of the present invention is useful in a new process comprising (1) applying an alkaline processing composition to the image-wise exposed photographic material comprising a support carrying at least one silver halide emulsion layer and at least one alkali-permeable layer (which may be the same layer as the one containing the silver halide) comprising said quinone-type compound that is initially immobile in an alkaline-permeable colloid medium, wherein said compound is capable of being reduced by a silver halide developing agent at a rate slower than that of image-wise developable silver halide in the material and in reduced state is capable under alkaline conditions of releasing a photographically useful group, (2) providing said developing agent for said photographic material during application of said alkaline processing composition under conditions to effect image-wise release of said photographically useful group inversely proportionally to the image-wise development of said silver halide in the photographic material, and (3) allowing the diffusion with said alkaline processing composition of the photographically useful group out of the layer in which it was originally incorporated to have it introduced image-wise in another layer.

In an embodiment for producing dye images, this invention relates to a photographic colour diffusion transfer process comprising:

(a) treating a photographic element in accordance with this invention with an alkaline processing composition in the presence of a silver halide developing agent to effect development of each of the exposed silver halide emulsion layers, thereby image-wise oxidizing the developing agent and as an inverse function of image-wise silver halide development reducing said immobile quinone-type compound(s) that in reduced state are capable of releasing (a) dye(s);

(b) maintaining said photographic material in the alkaline medium of the processing composition for a time sufficient to release said dye(s) in diffusible state from the reduced immobile compound(s); and (c) transferring at least a portion of said dye(s) to a non-light-sensitive layer acting as a receptor layer.

For in-camera processing the photosensitive material is preferably composed such that the photosensitive silver halide emulsion layer(s) is (are) negative-working and applied to the same support as the receptor layer so as to form an integral combination of light-sensitive layer(s) and a non light-sensitive layer receiver element preferably with an opaque layer, which is alkali-permeable, reflective to light and located between the receptor layer and the silver halide emulsion layer(s). In a process using such material the alkaline processing composition may be applied between the outer photosensitive layer of the photographic element and a cover sheet, which may be transparent and superposed before exposure.

In a modified embodiment, the dye-releasing compound can be incorporated into an alkali-permeable binder of a layer coated on a support other than the support of the silver halide emulsion layer(s) forming a receptor material separate from the light-sensitive material. Said receptor material can be processed by positioning it in interfacial contact with an image-wise exposed photographic silver halide material in the presence of an alkaline solution and a silver halide developing agent. In those areas where unoxidized silver halide developing agent reduces the initially immobile quinone-type compound capable of releasing a dye in alkaline medium when put in reduced state, a pattern of diffusible dye is formed. The diffusible dye is thereupon washed away leaving a reversed pattern of immobile dye in the receptor material. Likewise, if the initially immobile compound contains a tanning agent as the photographically useful moiety, it is possible to obtain a tanned image record in a receptor material in areas corresponding with those of the light-sensitive material where silver halide development does not take place, i.e. a positive tanned image record if a negative-working emulsion is used.

The photographic silver halide materials according to the present invention are processed in the presence of a silver halide developing agent, that has sufficient reducing power to convert oxidized nucleophilic groups such as oxidized hydroxyl groups on an aromatic nucleus from O=groups into hydroxyl groups again but at a rate slower than that of their own oxidation by imagewise developable silver halide, e.g. of a negative-working silver halide emulsion layer so that image differentiation by image-wise release of a photographically useful compound is still possible.

Photographic silver halide developing agents suitable for that purpose can be found by simple tests using them in combination with an elected set of silver halide and an immobile reducible quinone-type compound that can release in reduced state a photographically useful group under alkaline conditions.

Typical useful silver halide developing agents applicable in the present invention include: hydroquinone compounds, 1-arylpyrazolidin-3-one compounds, pyrogallol and substituted pyrogallol compounds and ascorbic acid or mixtures thereof. These developing agents of which useful representatives are disclosed in the U.S. Pat. No. 3,980,479, already mentioned hereinbefore, are preferably used in non-diffusible state when being with the compounds capable of releasing a photographically useful moiety in admixture in the same colloid layer, e.g. silver halide emulsion layer.

In a photographic element according to the invention and containing two or more silver halide emulsion layers, each silver halide emulsion layer containing a dye image-providing material or having the dye image-providing material present in a contiguous layer may be separated from the other silver halide emulsion layer(s) in the film unit by (an) interlayer(s), including e.g. gelatin, calcium alginate, or any of the colloids disclosed in U.S. Pat. No. 3,384,483 of Richard W. Becker, issued May 21, 1968, polymeric materials such as polyvinylamides as disclosed in U.S. Pat. No. 3,421,892 of Lloyd D. Taylor, issued Jan. 14, 1969, or any of those disclosed in French Patent Specification No. 2,028,236 filed Jan. 13, 1970 by Polaroid Corporation or U.S. Pat. Nos. 2,992,104 of Howard C. Haas, issued July 11, 1961 and 3,427,158 of David P. Carlson and Jerome L. Reid, issued Feb. 11, 1969.

According to an embodiment in the preparation of a multicolour diffusion transfer material according to the present invention, a water-permeable colloid interlayer dyed with a yellow non-diffusing dye or Carey Lea silver is applied below the blue-sensitive silver halide emulsion layer containing a yellow dye-releasing compound.

In certain embodiments of our invention and especially with integral format film units, an opacifying agent can be applied from a processing composition. Examples of opacifying agents include carbon black, barium sulphate, zinc oxide, barium stearate, silicates, alumina, zirconium oxide, zirconium acetyl acetate, sodium zirconium sulphate, kaolin, mica, titanium dioxide, organic dyes such as indicator dyes, nigrosines, or mixtures thereof in widely varying amounts depending upon the degree of opacity desired. In general, the concentration of opacifying agent should be sufficient to prevent further exposure of the film unit's silver halide emulsion or emulsions by ambient actinic radiation through the layer of processing composition, either by direct exposure through a support or by light piping from the edge of the element. For example, carbon black or titanium dioxide will generally provide sufficient opacity when they are present in the processing solution in an amount of from about 5 to 40% by weight. After the processing solution and opacifying agent have been distributed into the film unit, processing may take place out of the camera in the presence of actinic radiation in view of the fact that the silver halide emulsion(s) of the laminate is (are) appropriately protected against incident radiation, at one major surface by the opaque processing composition and at the remaining major surface by the opaque layer that is permeable to alkaline solutions. In certain embodiments, ballasted indicator dyes or dye precursors can be incorporated in a layer on the exposure side of the photosensitive layers; the indicator dye is preferably transparent during exposure and becomes opaque when contacted with the processing composition. Opaque binding tapes can also be used to prevent edge leakage of actinic radiation incident on the silver halide emulsion.

When titanium dioxide or other white pigments are employed as the opacifying agent in the processing composition, it may also be desirable to employ in cooperative relationship therewith a pH-sensitive opacifying dye such as a phthalein dye. Such dyes are light-absorbing or coloured at the pH at which image formation is effected and colourless or not light-absorbing at a lower pH. Other details concerning these opacifying dyes are described in French Patent Specification No. 2,026,927 filed Dec. 22, 1969 by Polaroid Corporation.

The substantially opaque, light-reflective layer, which is permeable to alkaline solutions, in the integral negative receiver film units of the present invention can generally comprise any opacifier dispersed in a binder as long as it has the desired properties. Particularly desirable are white light-reflective layers since they would be esthetically pleasing backgrounds on which to view a transferred dye image and would also possess the optical properties desired for reflection of incident radiation. Suitable opacifying agents include, as already mentioned with respect to the processing composition, titanium dioxide, barium sulphate, zinc oxide, barium stearate, silver flake, silicates, alumina, zirconium oxide, zirconium acetyl acetate, sodium zirconium sulphate, kaolin, mica, or mixtures thereof in widely varying amounts depending upon the degree of opacity desired. The opacifying agents may be dispersed in any binder such as an alkaline solution-permeable polymeric matrix such as, for example, gelatin, polyvinyl alcohol, and the like. Brightening agents such as the stilbenes, coumarins, triazines and oxazoles may also be added to the light-reflective layer, if desired. When it is desired to increase the opacifying capacity of the light-reflective layer, dark-coloured opacifying agents may be added to it, e.g., carbon black, nigrosine dyes, etc. Another technique to increase the opacifying capacity of the light-reflective layer is to employ a separate opaque layer underneath it comprising, e.g., carbon black, nigrosine dyes, etc., dispersed in a polymeric matrix that is permeable to alkaline solutions such as, e.g., gelatin, polyvinyl alcohol, and the like. Such an opaque layer would generally have a density of at least 4 and preferably greater than 7 and would be substantially opaque to actinic radiation. The opaque layer may also be combined with a developer scavenger layer if one is present. The light-reflective and opaque layers are generally 0.025 to 0.15 mm in thickness, although they can be varied depending upon the opacifying agent employed, the degree of opacity desired, etc.

The photosensitive substances used in this invention are preferably silver halide compositions and may comprise silver chloride, silver bromide, silver bromoiodie, silver chlorobromoiodide and the like, or mixtures thereof. The emulsions may be coarse- or fine-grain and can be prepared by any of the well-known procedures, e.g., single-jet emulsions, double-jet emulsions, such as Lippmann emulsions, ammoniacal emulsions, thiocyanate- or thioether-ripened emulsions such as those described in U.S. Pat. Nos. 2,222,264 of Adolph H. Nietz and Frederick J. Russell, issued Nov. 19, 1940, 3,320,069 of Bernard D. Illingsworth, issued May 16, 1967, and 3,271,157 of Clarence E. McBride, issued Sept. 6, 1966. Surface-image emulsions may be used or internal-image emulsions may be used such as those described in U.S. Pat. Nos. 2,592,250 of Edward Philip Davey and Edward Bowes Knott, issued Apr. 8, 1952, 3,206,313 of Henry D. Porter, Thomas H. James and Wesley G. Lowe, issued Sept. 14, 1965, and 3,447,927 of Robert E. Bacon and Jean F. Barbier, issued June 3, 1969. The emulsions may be regular-grain emulsions such as the type described by Klein and Moisar in J. Photogr. Sci., Vol. 12, No. 5, Sept./Oct., 1964, pp. 242-251. If desired, mixtures of surface- and internal-image emulsions may be used as described in U.S. Pat. No. 2,996,382 of George W. Luckey and John C. Hoppe, issued Aug. 15, 1961.

Negative-type or direct-positive emulsions may be used such as those described in U.S. Pat. Nos. 2,184,013 of John A. Leermakers, issued Dec. 19, 1939, 2,541,472 of William B. Kendall and George D. Hill, issued Feb. 13, 1951, 3,367,778 of Robert W. Berriman, issued Feb. 6, 1968, 3,501,307 of Bernard D. Illingsworth, issued Mar. 17, 1970, 2,563,785 of Charles F. Ives, issued Aug. 7, 1951, 2,456,953 of Edward Bowes Knott and Guy William Willis, issued Dec. 21, 1948, 2,861,885 of Edwin H. Land, issued Nov. 25, 1958, 3,761,276 of Francis John Evans, issued Sept. 25, 1973, 3,761,266 of Kirby Mitchell Milton, issued Sept. 25, 1973, 3,736,140 of Susan Starr Collier and Paul Brewster Gilman Jr., issued May 29, 1973, and 3,730,723 of Paul Brewster Gilman Jr., Ronald George Raleigh and Thaddeus Donald Koszelak, issued May 1, 1973, and United Kingdom Pat. No. 723,019 filed Feb. 5, 1952 by Gevaert Photo-Producten N.V.

The silver halide emulsions useful in our invention are well-known to those skilled in the art. More details about their composition, preparation and coating are described, e.g., in Product Licensing Index, Vol. 92, December 1971, publication 9232, p. 107-109.

Generally speaking, the silver halide emulsion layers in the invention comprise photosensitive silver halide dispersed in gelatin and are about 0.2 to 2 $\mu$m thick; the dye image-providing materials are dispersed in a polymeric binder permeable to alkaline solutions, such as gelatin, to form a separate layer of about 1 to 7 $\mu$m thick, and the polymeric interlayers permeable to alkaline solutions, e.g., gelatin, are about 1 to 5 $\mu$m thick. Of course these thicknesses are approximate only and may be modified according to the product desired.

The support for the photographic elements of this invention may be any material as long as it does not deleteriously affect the photographic properties of the film unit and is dimensionally stable. Typical flexible sheet materials are paper supports, e.g. coated at one or both sides with an $\alpha$-olefin polymer, e.g. polyethylene, or include cellulose nitrate film, cellulose acetate film, poly(vinyl acetal) film, polystyrene film, poly(ethylene terephthalate) film, polycarbonate film, poly-$\alpha$-olefins such as polyethylene and polypropylene film, and related films or resinous materials. The support is usually about 0.05 to 0.15 mm thick.

Any material can be employed as the image-receiving layer in this invention as long as the desired function of mordanting or otherwise fixing the dye images will be obtained. The particular material chosen will, of course, depend upon the dye to be mordanted. If acid dyes are to be mordanted, the image-receiving layer can be composed of or contain basic polymeric mordants such as polymers of aminoguanidine derivatives of vinyl methyl ketone such as described in U.S. Pat. No. 2,882,156 of Louis M. Minsk, issued Apr. 14, 1959, and basic polymer mordants and derivatives, e.g. poly-4-vinylpyridine, the 2-vinylpyridine polymer metho-p-toluene sulphonate and similar compounds described in U.S. Pat. No. 2,484,430 of Robert H. Sprague and Leslie G. Brooker, issued Oct. 11, 1949, the compounds described in the published German Patent Application No. 2,200,063 filed Jan. 11, 1971 by Agfa-Gevaert A.G. Suitable mordanting binders include, e.g. guanylhydrazone derivatives of acyl styrene polymers, as described e.g. in published German Patent Specification No. 2,009,498 filed Feb. 28, 1970 by Agfa-Gevaert A.G. In general, however, other binders, e.g. gelatin, would be added to the last-mentioned mordanting binders. Effective mordanting compositions are long-chain quaternary ammonium or phosphonium compounds or ternary sulphonium compounds, e.g. those described in U.S. Pat. Nos. 3,271,147 of Walter M. Bush and 3,271,148 of Keith E. Whitmore, both issued Sept. 6, 1966, and cetyltrimethyl-ammonium bromide. Certain metal salts and their hydroxides that form sparingly soluble compounds with the acid dyes may be used too. The dye mordants are dispersed in one of the usual hydrophilic binders in the image-receiving layer, e.g. in gelatin, polyvinylpyrrolidone or partly or completely hydrolysed cellulose esters.

Generally, good results are obtained when the image-receiving layer, which is preferably permeable to alkaline solution, is transparent and about 4 to about 10 μm thick. This thickness, of course, can be modified depending upon the result desired. The image-receiving layer may also contain ultraviolet-absorbing materials to protect the mordanted dye images from fading, brightening agents such as the stilbenes, coumarins, triazines, oxazoles, dye stabilizers such as the chromanols, alkyl-phenols, etc.

Use of pH-lowering material in the dye-image-receiving element of a film unit according to the invention will usually increase the stability of the transferred image. Generally, the pH-lowering material will effect a reduction of the pH of the image layer from about 13 or 14 to at least 11 and preferably 5–8 within a short time after imbibition. For example, polymeric acids as disclosed in U.S. Pat. No. 3,362,819 of Edwin H. Land, issued Jan. 9, 1968 or solid acids or metallic salts, e.g. zinc acetate, zinc sulphate, magnesium acetate, etc., as disclosed in U.S. Pat. No. 2,584,030 of Edwin H. Land, issued Jan. 29, 1952, may be employed with good results. Such pH-lowering materials reduce the pH of the film unit after development to terminate development and substantially reduce further dye transfer and thus stabilize the dye image.

An inert timing or spacer layer may be employed in practice over the pH-lowering layer, which "times" or controls the pH reduction depending on the rate at which alkali diffuses through the inert spacer layer. Examples of such timing layers include gelatin, polyvinyl alcohol or any of the colloids disclosed in U.S. Pat. No. 3,455,686 of Leonard C. Farney, Howard G. Rogers and Richard W. Young, issued July 15, 1969. The timing layer may be effective in evening out the various reaction rates over a wide range of temperatures, e.g., premature pH reduction is prevented when imbibition is effected at temperatures above room temperature, e.g. at 35° to 37° C. The timing layer is usually about 2.5 μm to about 18 μm thick. Especially good results are obtained when the timing layer comprises a hydrolysable polymer or a mixture of such polymers that are slowly hydrolysed by the processing composition. Examples of such hydrolysable polymers include polyvinyl acetate, polyamides, cellulose esters, etc.

An alkaline processing composition employed in this invention can be a conventional aqueous solution of an alkaline material, e.g. sodium hydroxide, sodium carbonate or an amine such as diethylamine, preferably possessing a pH beyond 11.

According to one embodiment the alkaline processing liquid contains the diffusible developing agent that effects the reduction of the complexed silver halide, e.g. ascorbic acid or a 3-pyrazolidinone developing agent such as 1-phenyl-4-methyl-3-pyrazolidinone.

The alkaline processing composition employed in this invention may also contain a desensitizing agent such as methylene blue, nitro-substituted heterocyclic compounds, 4,4'-bipyridinium salts, etc., to insure that the photosensitive element is not further exposed after it is removed from the camera for processing.

The solution also preferably contains a viscosity-increasing compound such as a high-molecular-weight polymer, e.g. a water-soluble ether inert to alkaline solutions such as hydroxyethylcellulose or alkali metal salts of carboxymethylcellulose such as sodium carboxymethylcellulose. A concentration of viscosity-increasing compound of about 1 to about 5% by weight of the processing composition is preferred. It will impart thereto a viscosity of about 100 cP to about 200,000 cP.

Processing may proceed in a tray developing unit as is present, e.g., in an ordinary silver complex diffusion transfer (DTR) apparatus in which the contacting with a separate dye image-receiving material is effected after a sufficient absorption of processing liquid by the photographic materials has taken place. A suitable apparatus for said purpose is the COPYPROOF CP 38 (trade name) DTR-developing apparatus. COPYPROOF is a trade name of Agfa-Gevaert, Antwerpen/Leverkusen.

According to other embodiments wherein the receptor layer is integral with the photosensitive layer(s) the processing liquid is applied from a rupturable container or by spraying.

The rupturable container that may be employed in this invention may be of the type disclosed in U.S. Pat. Nos. 2,543,181 of Edwin H. Land, issued Feb. 27, 1951, 2,643,886 of Ulrich L. di Ghilini, issued June 30, 1953, 2,653,732 of Edwin H. Land, issued Sept. 29, 1953, 2,723,051 of William J. McCune Jr., issued Nov. 8, 1955, 3,056,492 and 3,056,491, both of John E. Campbell, issued Oct. 2, 1962, and 3,152,515 of Edwin H. Land, issued Oct. 13, 1964. In general such containers comprise a rectangular sheet of fluid- and air-impervious material folded longitudinally upon itself to form two walls that are sealed to one another along their longitudinal and end margins to form a cavity in which processing solution is contained.

While the alkaline processing composition used in this invention can be employed in a rupturable container, as described previously, to facilitate conveniently the introduction of processing composition into the film unit, other means of discharging processing composition within the film unit could also be employed, e.g., means injecting processing solution with communicating members similar to hypodermic syringes, which are attached either to a camera or camera cartridge, as described in U.S. Pat. No. 3,352,674 of Donald M. Harvey, issued Nov. 14, 1967.

The main aspect of the present invention is the use of quinone type compounds from which by reduction and in alkaline medium a dye is released as photographically useful fragment. This is the reason why, in the following, mainly reference is made to colour providing compounds. The invention, however, is not at all limited to this aspect and it should be kept in mind that for various other purposes other photographically useful fragments may be present in these compounds instead of dyes or dye precursors.

The following examples further illustrate the invention. All percentages and ratios are by weight, unless otherwise mentioned.

EXAMPLE 1

A subbed water-resistant paper support consisting of a paper sheet of 110 g/sq.m coated at both sides with a polyethylene stratum of 15 g/sq.m was treated with a corona discharge and thereupon coated in the mentioned order with the following layers, the amounts relating to 1 sq.m of material:

(1) an alkali-permeable colloid layer containing after drying per sq.m:
gelatin: 3 g
a cyan dye-releasing compound in quinone-form prepared as described hereinafter. The quinone-compound was incorporated before coating in an aqueous gelatin solution in the form of droplets comprising the quinone compound in a mixture of tricresyl phosphate and N-methylpyrrolidone in a 1/1/1 ratio: 0.5 g
(2) a silver chloride emulsion layer comprising per sq.m:
silver chloride: 2 g
ascorbic acid: 0.8 g
gelatin: 2.5 g
(3) an antistress layer containing per sq.m:
gelatin: 2 g Processing A sheet of the obtained photographic material was exposed through a grey wedge having a constant 0.1 and thereupon contacted with the receptor material described hereinafter in the COPYPROOF CP 38 (trade name) diffusion transfer processing apparatus containing in its tray an aqueous solution comprising per liter: 15 g of sodium hydroxide, 1 g of 1-phenyl-3-pyrazolidinone and 1 g of potassium bromide.

After a contact time of 2 min the receptor material and light-sensitive material were peeled apart and dried. The maximum optical density of the positive cyan dye image obtained in the receptor material was 2.12.

Composition of the receptor material

To the same support as described for the above light-sensitive material a coating having the following composition was applied per sq.m:
gelatin: 5 g
triphenyl-n-hexadecylphosphonium bromide: 2 g Preparation of the quinone form of the cyan dye-releasing compound 2.5 g of the following compound

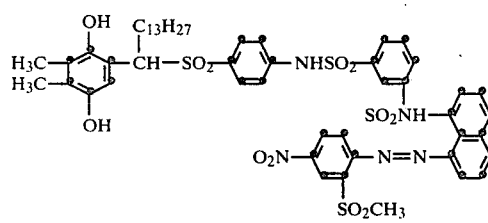

(compound No. 5 of the table hereinafter) (prepared as compound 5 in the Belgian Pat. No. 861,241 already mentioned hereinbefore) were refluxed in 50 ml of anhydrous ethanol in the presence of 0.3 g of p-benzoquinone for 1 h. The solution was cooled and the obtained crystalline precipitate separated by suction-filtering. Yield: 2.45 g of the cyan dye-releasing quinone-compound having the following structural formula:

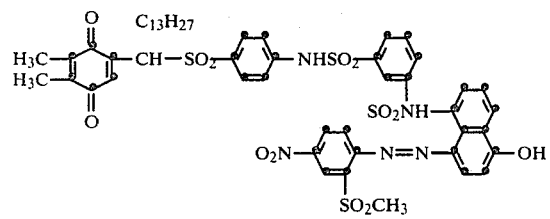

EXAMPLE 2

The light-sensitive material was built up as described in Example 1 with the difference, however, that the ascorbic acid was left out of the composition.

The exposure and processing proceeded as in Example 1 with the difference, however, that the processing liquid effecting the development had the following composition:
sodium hydroxide: 15 g
1-phenyl-3-pyrazolidinone: 1 g
potassium bromide: 1 g
ascorbic acid: 2 g
water up to: 1 l.

After a diffusion transfer of 2 min in contact with the receptor material as described in Example 1 a positive cyan wedge image with a maximum optical density of 2.25 was obtained.

EXAMPLE 3

Composition of the light-sensitive material

A support as described in Example 1 was coated with the following layers:
(1) a silver chloride emulsion layer comprising per sq.m:
silver chloride: 2.5 g
the cyan dye-releasing compound in quinone-form of Example 1: 0.5 g
1-phenyl-3-pyrazolidinone: 0.2 g
ascorbyl palmitate applied from a solution prepared as described hereinafter: 1.5 g
gelatin: 6 g
(2) an antistress layer containing per sq.m:
gelatin: 2 g Preparation of the ascorbyl palmitate solution 40 g of ascorbyl palmitate were added with vigorous stirring to a mixture of:
50% aqueous mixture of

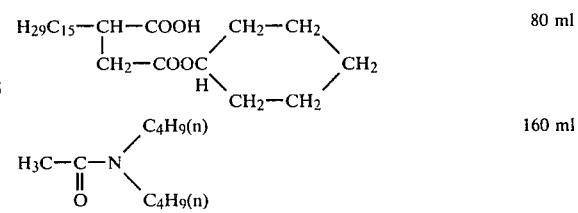 80 ml 160 ml distilled water: 640 ml
gelatin: 40 g
10% aqueous solution of

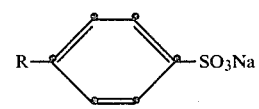

R=alkyl chain with $C_{10}-C_{13}$ atoms: 40 ml

The exposure and processing of the light-sensitive material proceeded as in Example 1 with the difference, however, that the processing liquid contained 15 g of sodium hydroxide, 1 g of potassium bromide and 10 g of sodium sulphite per liter of water.

After a diffusion transfer of 2 min in contact with the receptor material as described in Example 1 a positive cyan wedge image with a maximum optical density 1.75 was obtained.

EXAMPLE 4

Composition of light-sensitive material

A subbed water-resistant paper support consisting of a paper sheet of 110 g/sq.m coated at both sides with a polyethylene stratum of 15 g/sq.m was treated with a corona discharge and thereupon coated in the mentioned order with the following layers, the amounts relating to 1 sq.m of material:

(1) a red-sensitive silver bromide iodide emulsion layer incorporating an amount of silver halide corresponding with 1.75 g of silver, 4 g of gelatin, 0.15 g of 1-phenyl-4-methyl-3-pyrazolidinone, 0.7 g of ascorbyl palmitate added from the solution prepared as described above and 0.35 g of the quinone compound corresponding with the cyan dye releasing hydroquinone No. 39 of the Table hereinafter, (2) a magenta filter layer containing 2 g of gelatin and 1 g of Pigment Red 146 (Colour Index No. 11,000) sold under the trade name COLANYL CARMIN FBB31 by Farbwerke Hoechst A. G., W.Germany;

(3) a green-sensitive silver bromide iodide emulsion layer incorporating an amount of silver halide corresponding with 2.2 g of silver, 5 g of gelatin, 0.15 g of 1-phenyl-4-methyl-3-pyrazolidinone, 0.9 g of ascorbyl palmitate added from the solution prepared as described above and 0.38 g of the quinone compound corresponding with the magenta dye releasing hydroquinone No. 38 of the Table hereinafter;

(4) a yellow filter layer containing 2 g of gelatin and 1.2 g of Pigment Yellow 83 (Colour Index No. 20,000) sold under the trade name PERMANENT-GELB HR COLANYL TEIG by Farbwerke Hoechst A. G., W.Germany;

(5) a blue-sensitive silver bromide iodide emulsion layer incorporating an amount of silver halide corresponding with 2.2 g of silver, 5 g of gelatin, 0.15 g of 1-phenyl-4-methyl-3-pyrazolidinone, 0.9 g of ascorbyl palmitate added from the solution prepared as described above, and 0.47 g of the quinone compound corresponding with the yellow dye releasing hydroquinone No. 37 of the Table hereinafter;

(6) an antistress layer containing 1.5 g of gelatin.

Processing

A sheet of the obtained photographic material was exposed through a multicolour image transparency and thereupon contacted with the receptor material described hereinafter in the COPYPROOF CP 38 (trade name) diffusion transfer processing apparatus containing in its tray an aqueous solution comprising per liter: 15 g of sodium hydroxide, 1 g of 1-phenyl-3-pyrazolidinone and 1 g of potassium bromide.

After a contact time of 20 min the receptor material and light-sensitive material were peeled apart and dried. In the receptor material a positive multicolour image of the original transparency was obtained.

Composition of the receptor material

To the same support as described for the above light-sensitive material a coating having the following composition was applied per sq.m:
gelatin: 5 g
triphenyl-n-hexadecylphosphonium bromide: 2 g Analogously to the above light-sensitive material other materials are built up by using other cyan dye releasing quinone-compounds, other magenta dye releasing quinone-compounds and other yellow dye releasing quinone-compounds. Such particular quinone-type dye-releasing compounds are represented in the Table in their hydroquinone form or free amine ($H_2N-$) form and also identified by the colour of the released dye.

TABLE

| No. of compound | Structural formula | Colour of released dye |
|---|---|---|
| (1) | $H_2C-SO_2$—⟨⟩—$NH-SO_2$—⟨$OCH_3$⟩—$N=N-HC$—$C-CH_3$, $O=C$, $N$, (phenyl); HO—⟨⟩—OH, $C_{14}H_{29}$ | yellow |
| (2) | $CH_2-NO_2$, $HC-SO_2$—⟨⟩—$NHSO_2$—⟨⟩—$NH-CO-CH_3$, $N=N$—⟨Cl⟩; HO—⟨⟩—OH, $C_{14}H_{29}$ | magenta |
| (3) | OH, $C_{13}H_{27}$, $CH_3$—⟨⟩—$CH-SO_2$—⟨$OCH_3$⟩, $CH_3$, OH, $N=N$—⟨⟩—OH | magenta |

TABLE-continued

| No. of compound | Structural formula | Colour of released dye |
|---|---|---|
| (4) | | magenta |
| (5) | | cyan |
| (6) | | yellow |
| (7) | | cyan |
| (8) | | magenta |
| (9) | | cyan |
| (10) | | magenta |

TABLE-continued

| No. of compound | Structural formula | Colour of released dye |
|---|---|---|
| (11) | | yellow |
| (12) | | magenta |
| (13) | | magenta |
| (14) | | yellow |
| (15) | | magenta |
| (16) | | magenta |
| (17) | | magenta |

TABLE-continued

| No. of compound | Structural formula | Colour of released dye |
| --- | --- | --- |
| (18) | | cyan |
| (19) | | cyan |
| (20) | | yellow |
| (21) | | magenta |
| (22) | | magenta |
| (23) | | yellow |

TABLE-continued

| No. of compound | Structural formula | Colour of released dye |
|---|---|---|
| (24) | | magenta |
| (25) | | yellow |
| (26) | | magenta |
| (27) | | cyan |
| (28) | | cyan |
| (29) | | yellow |

TABLE-continued

| No. of compound | Structural formula | Colour of released dye |
| --- | --- | --- |
| (30) | | yellow |
| (31) | | magenta |
| (32) | | cyan |
| (33) | | magenta |
| (34) | | cyan |
| (35) | | magenta |

TABLE-continued

| No. of compound | Structural formula | Colour of released dye |
|---|---|---|
| (36) | | magenta |
| (37) | | yellow |
| (38) | | magenta |
| (39) | | cyan |
| (40) | | yellow |

The preparation of some of the compounds listed in the Table above is described in the following by way of example. The other compounds may be prepared using slightly modified procedures.

Preparation of compound No. 1

(a) 2-tetradecanoylhydroquinone may be prepared as described by Armstrong et al, J.Amer.Chem.Soc. 82, 1928 (1960) for the case of 2-stearoylhydroquinone. Melting point: 101°–103° C.

(b) 2-tetradecylhydroquinone

The carbonyl compound 1a was subjected to the Wolff-Kishner reduction:

64 g of 2-tetradecanoylhydroquinone was refluxed for two hours together with 30 g of hydrazine hydrate, 45 g of powdered KOH and 300 ml of triethyleneglycol. Thereafter the reflux condenser was replaced by a descending cooler and the mixture was heated for four hours up to 195° C. When cool the mixture was poured into 800 ml of water and the suspension obtained was several times extracted with ether. The combined extracts were washed with water and evaporated. The residue crystallised from 250 ml of benzene.

Yield: 22 g. Melting point: 108°–109° C.

(c) 2-tetradecyl-5-formyl-hydroquinone.

4.5 ml of titanium-IV-chloride were added at 5° C. under a protective atmosphere of nitrogen to a suspension of 6.12 g of 1b in 120 ml of dichlormethane. 6.3 g of α,α-dichlorodimethylether were added without cooling. The obtained solution was stirred at 35° C. until the evolution of hydrogen chloride was finished. The mixture was decomposed by the addition of some crushed ice and 120 ml of 5% hydrochloric acid and three times extracted with ether. The combined ether extracts were washed with 2% sodium carbonate solution and with water. The organic solution was dried with Na$_2$SO$_4$ and evaporated. The yellowish-brown residue was recrystallized from ligroin.

Yield: 3 g. Melting point: 66°–69° C.

(d) 2-tetradecyl-5-hydroxymethyl-hydroquinone.

A solution of 0.31 g of sodium borohydride in 2 ml of water were added with stirring at 40° C. and under protective nitrogen to a solution of 2.45 g of the aldehyde 1 c in 30 ml of methanol. After 20 min the solution was poured out into 100 ml of 5% sulfuric acid. The precipitate formed was suction filtered and dried. Recrystallization was made from butyl chloride.

Yield: 1.95 g. Melting point: 106°–108° C.

(e) 4-[4-(1-phenyl-3-methyl-pyrazolone-(5)-yl-(4)-azo)-3-methoxybenzenesulphonamido]-benzenesulphinic acid 4.07 g of 4-(1-phenyl-3-methyl-pyrazolone-(5)-yl-(4)-azo)-3-methoxy-benzenesulphonylchloride, 1.6 g of 4-aminobenzenesulphinic acid and 1.2 g of dimethylaniline were stirred in 6 ml of dimethylformamide for 3 hours at 20° C. The solution was poured out into 200 ml of 2 N hydrochloric acid. The dye was salted out as sulphinic acid.

Yield: 4 g.

(f) Compound No. 1

A solution of 1.68 g of the carbinol compound 1 d in 90 ml of acetic acid was mixed with a solution of 2.64 g of the sulphinic acid 1 e and 0.56 g of sodium acetate in 25 ml of ethanol (80%). The mixture after addition of 0.2 ml of concentrated sulphuric acid was refluxed for 4 hours. The obtained solution was poured out into water and extracted with ethyl acetate. The combined extracts were washed with 5% sodium acetate solution and with water until the aqueous phase was colourless. After removal of the solvent by evaporation the residue was heated with a 1:1 mixture of butylchloride and ligroin. The residue crystallized on trituration with butyl chloride and was recrystallized from ethyl acetate.

Yield: 0.65 g. Melting point: 165°–170° C.

Preparation of compound No. 3

(a) 2,3-dimethyl-5-tetradecanoyl-hydroquinone.

A solution of 56 g 2,3-dimethylhydroquinone [Acta Pharm. Suecica 5, 215 (1968)] and 147.5 g of myristic acid in 200 ml of dichloromethane was saturated at 35°–40° C. with boron trifluoride. After standing over night the solution was refluxed for 2 hours. The mixture was stirred into a solution of 113 g of sodium acetate in 1000 ml of water. After 30 min the layer of dichloromethane was separated and 2 times washed with 5% sodium carbonate. After removal of the organic solvent the residue was recrystallized from ligroin.

Yield: 80 g. Melting point: 101°–102° C.

(b) 2,3-dimethyl-5-α-hydroxytetradecyl-hydroquinone, 6.4 g of sodium borohydride dissolved in 40 ml of water were added dropwise at 30° C. with stirring to a solution of 70 g of the keto compound 3 a in 600 ml of methanol. By cooling the temperature was kept below 30° C. After 30 min the mixture was diluted with 1 l of water and acidified with diluted sulphuric acid. The precipitate was taken up in ethylacetate and the organic layer was separated. After removal of the ethyl acetate the residue was purified by heating it with butyl chloride.

Yield: 60 g. Melting point: 132° C.

(c) 2-methoxy-5-(β-hydroxynaphthylazo)-benzene-sulphuric acid sodium salt.

1.87 g of 2-methoxy-5-amino-benzenesulphinic acid were dissolved in 18 ml of water together with 0.4 g of NaOH. After addition of 0.7 g of sodium nitrite and 15 g of ice 3 ml of concentrated hydrochloric acid were slowly added with stirring. The solution was stirred for another 15 min and then added dropwise slowly with stirring at 5°–8° C. to a solution of 1.44 g of β-naphthol and 2.5 g of sodium carbonate in 30 ml of water. After stirring for one hour at 5°–8° C. the formed precipitate was suction filtered, washed with 10% sodium chloride solution and dried on clay.

Yield: 3.2 g.

(d) Compound No. 3

1.75 g of the carbinol 3 b were dissolved in 60 ml of acetic acid at 60° C. and a solution of 2 g of the dye sulphinate 3 c in 25 ml of water was added. The mixture was stirred at 50° C. for 30 min and then cooled. The precipitate was separated from the solvent by decanting and taken up in ethyl acetate. The concentrated ethyl acetate solution was washed with water several times and the compound No. 3 was precipitated by addition of ligroin.

Yield: 1.5 g. Melting point: 149°–151° C.

Preparation of compound No. 4

(a) 4-[4-acetamido-5-hydroxy-6-(2-chlorphenylazo)-naphthalene-(1)-sulphamido]-benzenesulphinic acid A mixture of 2.19 g of 4-acetamido-5-hydroxy-6-(2-chlorphenylazo)-naphthalene-(1)-sulphonylchloride, 0.79 g of 4-aminobenzenesulphinic acid and 0.6 g of dimethylaniline in 30 ml of dimethylformamide was stirred at 20° C. for 2.5 h and then stirred into 150 ml of 2 N hydrochloric acid. The precipitate was suction filtered, washed with diluted hydrochloric acid, pressed on clay and dried.

Yield: 2.4 g.

(b) Compound No. 4

2.23 g of dye sulphinic acid 4 a were dissolved in 40 ml of 3 N acetic acid together with 0.5 g of anhydrous sodium acetate and mixed with a solution of 1.4 g of the carbinol 3 b in 50 ml of acetic acid. The mixture was stirred at 50° C. for 1.5 h. After cooling the precipitate was suction filtered, washed with acetic acid and dried. The raw material was then heated with 30 ml of ethyl acetate; undissolved was removed by filtration and the filtrate was concentrated. After standing for several hours the purple compound no. 4 precipitated from the concentrated residue.

Yield: 0.9 g. Melting point: 167°–170° C.

Preparation of compound No. 5

(a) 4-{3-[5-hydroxy-8-(2-methylsulphonyl-4-nitrophenylazo)naphthyl-(1)-aminosulphonyl]-benzene sulphonamido}benzenesulphinic acid This compound was prepared similarly as compound 4 a. Instead of 2.19 g of 4-acetamido-5-hydroxy-6-(2-chlorophenylazo)-naphthalene-(1)-sulphonylchloride. 3.13 g of 3-[5-hydroxy-8-(2-methylsulphonyl-4-nitrophenylazo)naphthyl-(1)-aminosulphonyl]-benzene sulphonylchloride were used.

Yield: 3.6 g.

(b) Compound No. 5

This compound was prepared in an analogeous manner as compound No. 4. 3 g of dye sulphinic acid 5 a were used instead of 2.23 g of dye sulphinic acid 4 a.

Yield: 0.95 g after recrystallization from ethyl acetate/ligroin.

Preparation of compound No. 6

(a) 4-[4-(1-phenyl-3-N-methylcarbamoyl-pyrazolon-(5)-yl-(4)-azobenzenesulphonamido]-benzene sulphinic acid.

This compound was prepared similarly as sulphinic acid 4 a. 2.1 g of 4-(1-phenyl-3-N-methylcarbamoyl-pyrazolone-(5)-yl-(4)-azo)-benzenesulphonylchloride were reacted with 0.79 g of 4-aminobenzene sulphinic acid.

(b) Compound No. 6

This yellow dye was prepared in an analogous manner as compound 4, from 2.16 g of the dye sulphinic acid 6 a described above.

Yield: 0.93 g. Melting point: 128°–131° C.

Preparation of compound No. 15

(a) 5-acetyl-2-octadecylhydroquinone.

Into a solution of 108.6 g (0.3 mole) of 2-octadecylhydroquinone, 27 g of glacial acetic acid and 300 ml of ethylene chloride, boron trifluoride was introduced with stirring at 40°–45° C. until saturation. After allowing to stand overnight the reaction mixture was refluxed on the steambath for 6 h and cooled, whereupon the mixture was poured with stirring into a solution of 80 g of sodium acetate in 740 ml of water. After 30 min the organic phase was taken up in ethylene chloride and washed with a 5% by weight aqueous sodium carbonate solution and water. The solution was concentrated to a volume of 400 ml and diluted with petroleum ether. The precipitate formed by standing overnight at 5° C. was filtered with suction and recrystallized from n-butyl chloride.

Yield: 83 g. Melting point: 99°–101° C.

(b) 6-(α-hydroxyethyl)-2-octadecylhydroquinone 40.4 g (0.1 mole) of the ketone prepared in (a) were dissolved in 400 ml of methanol. To this solution a solution of 3.2 g of sodium borohydride in 20 ml of water was slowly added with stirring at 40° C. After 20 min the solution was poured with stirring into 1 l of water and acidified with dilute sulphuric acid. The precipitate formed was filtered with suction and taken up in ethyl acetate. The solution obtained was shaken with water several times. The residue left after evaporation of the solvent was recrystallized from n-butyl chloride.

Yield: 30 g. Melting point: 66°–69° C.

(c) 4-(1-hydroxy-2-N,N-diethylsulphamoyl-5-methylsulphonamidonaphthyl-4-azo)-benzenesulphinic acid.

17.9 g (0.1 mole) of the sodium salt of 4-aminobenzenesulphinic acid and 7 g of sodium nitrite were dissolved in 120 ml of water. The solution was cooled in ice-water and 100 g of ice were added. Then 28 ml of strong hydrochloric acid were added under nitrogen atmosphere. The mixture formed was rapidly poured with stirring into a solution of 37.5 g (0.1 mole) of 1-hydroxy-2-N,N-diethylsulphamoyl-5-methylsulphonamidonaphthalene and 37 g of sodium carbonate in 250 ml of water and 70 ml of acetone. After 45 min the deeply coloured solution was mixed with 250 ml of acetic acid whereupon the precipitate obtained was filtered with suction and dried. Yield: 55 g.

(d) Compound No. 15.

2.05 g of the carbinol prepared under (b), 3.3 g of the dye sulphinic acid prepared under (c) and 2.5 g of anhydrous magnesium sulphate were heated with stirring until boiling in 65 ml of acetonitrile and 5 ml of acetic acid for 2 h. The mixture was filtered while still hot. After standing overnight 2.9 g of red precipitate were deposited. It was purified by dissolving in 10 parts of dimethylformamide and by stirring for 30 min after the addition of 0.5 g of ascorbic acid. The dye was precipitated again by adding water and filtered with suction. Yield: 2.5 g.

Preparation of compound No. 16

(a) 5-(α-hydroxy-α-methylethyl)-2-octadecylhydroquinone.

A solution of 20.2 g (0.05 mole) of the ketone prepared in example 15(a) in 150 ml of ether was dropwise and slowly added with stirring at boiling point to 101 ml of a 40% by weight solution of methyl magnesium bromide in ether. After refluxing for 2 h the reaction mixture was poured into a mixture of ice-water and glacial acetic acid, whereupon the organic phase was separated. The solution in ether was shaken several times with ammonium chloride solution. After the ether was distilled an oily residue was left, which was made to crystallize by means of petroleum benzine.

Yield: 18.5 g. Melting point: 85°–87° C.

(b) Compound No. 16.

The preparation of compound 16 proceeded analogously to compound 15 under item 15d by making to react 2.1 g of the carbinol prepared according to example 16(a) with 3.3 g of the dye sulphinic acid prepared according to 15(c).

Yield: 1.8 g.

Preparation of compound No. 17

Step 1

2,3-dimethyl-6-tetradecanoyl-hydroquinone

Boron trifluoride was introduced with vigorous refluxing (bath temperature 50° C.) into a mixture of 138 g (1 mole) of 2,3-dimethylhydroquinone, 370 g (1.62 moles) of myristic acid and 700 ml of methylene chloride until saturation. After standing overnight the reaction mixture was decomposed by pouring into 3 l of a 10% by weight sodium acetate solution with stirring. The methylene chloride was evaporated by means of steam. The residual oily layer solidified after cooling to a melt cake that was isolated by decantation. It was melted up and added with stirring to 2 l of high-boiling benzine. The precipitate was filtered with suction and washed with benzine (boiling range: 50°–75° C.). After being dried the precipitate was stirred with acetonitrile and filtered with suction.

Yield: 260 g. Melting point: 100°–101° C.

Step 2

4-hydroxy-2,3-dimethyl-6-tetradecanoylphenyl allyl ether 43 g of allyl bromide were dropwise added with gentle boiling within 2 h to a mixture of 105 g of the ketone of step 1, 63 g of potassium carbonate and 1200 ml of methyl ethyl ketone. After 9 h of boiling the mixture was cooled to 30° C. and 200 ml of water were added. The aqueous layer was separated. Then the organic layer was shaken once with a 25% by weight sodium chloride solution and filtered off, whereupon the solvent was distilled. The residue was stirred into 1 l of methanol and filtered with suction.

Yield: 95 g. Melting point: 65°–66° C.

Step 3

2,3-dimethyl-5-allyl-6-tetradecanoylhydroquinone 90 g of the allyl ether of step 2 were heated to 210° C. under nitrogen atmosphere within 2 h. After cooling the melt was dissolved in 300 ml of benzine (boiling range: 50°–75° C.) and placed in a cool place. The precipitate formed was filtered with suction the next day.

Yield: 73 g. Melting point: 68°–69° C.

Step 4

2,3-dimethyl-5-propyl-6-tetradecanoylhydroquinone 16.2 g of the above allyl compound were hydrogenated in a shaking autoclave in the presence of Raney nickel under standard conditions of temperature and pressure. After elimination of the Raney nickel the alcohol was distilled and the residue was recrystallized from 300 ml of benzine.

Yield: 15 g. Melting point: 69°–79° C.

Step 5

2,3-dimethyl-5-propyl-6-$\alpha$-hydroxytetradecylhydroquinone 14 g of the keto-compound of step 4 were dissolved in 390 ml of methanol and slowly mixed with stirring under nitrogen atmosphere with a solution of 1.97 g of sodium borohydride in 24 ml of water. After 30 min the mixture was slightly acidified with glacial acetic acid and poured with stirring into a solution of 2.5 ml of sulphuric acid in 270 ml of water. The precipitate formed was filtered with suction and recrystallized from methanol.

Yield: 10.5 g. Melting point: 140°–142° C.

Step 6

Dye sulphinic acid 4-(4'-hydroxy-3'-N,N-diethylsulphamyl-8'-sulphonamidonaphthyl-1'-azo)-benzenesulphinic acid 11.5 g of the sodium salt of 4-aminobenzenesulphinic acid and 4.4 g of sodium nitrite were dissolved in 70 ml of water under nitrogen atmosphere, mixed with 85 g of finely crushed ice and 18 ml of strong hydrochloric acid. The diazonium salt solution was poured at once with stirring into a solution of 25 g of 1-hydroxy-2-N,N-diethylsulphamyl-5-methylsulphonamidonaphthalene, 23.15 g of sodium carbonate, 130 ml of water and 45 ml of acetone. After 30 min the dye solution was poured with stirring into 200 ml of glacial acetic acid, whereupon the precipitated dye was filtered with suction, and dried in a vacuum exsiccator.

Yield: 32 g of crude dye, which was used as such for the transformation to compound No. 17.

Step 7

Compound No. 17

A solution of 7 g of dye sulphinic acid of step 6, 1.5 g of anhydrous sodium acetate, 120 ml of glacial acetic acid and 40 ml of water were added to a 60° C. hot solution of 4 g of the carbinol compound of step 5 in 300 ml of glacial acetic acid, which was heated to 60° C. The mixture obtained was heated at 90° C. under nitrogen atmosphere for 2 h. Shortly thereafter the dye began to precipitate. After having been cooled to 60° C. the precipitate formed was filtered with suction and washed with glacial acetic acid. It was purified by stirring with methanol.

Yield: 5.6 g.

Preparation of compound No. 27

Step 1

2-methyl-5-hexadecanoylhydroquinone

Boron trifluoride was introduced with vigorous refluxing until saturation into a mixture of 27.2 g of palmitic acid, 13.7 g of 2-methylhydroquinone and 45 ml of methylene chloride. After standing overnight the mixture was refluxed for another hour and then decomposed with stirring in a solution of 25 g of sodium acetate in 220 ml of water. After 45 min the solution in methylene chloride was separated and evaporated. The residue was stirred with methanol, filtered with suction and recrystallized from n-chlorobutane.

Yield: 21 g. Melting point: 90°–93° C.

Step 2:

4-hydroxy-2-methyl-5-hexadecanoylphenyl allyl ether

Under nitrogen atmosphere a mixture of 17.5 g of the keto-compound of step 1, 10.2 g of potassium carbonate and 200 ml of methyl ethyl ketone was refluxed with stirring together with 6.9 g of allyl bromide for 1 hour. After a total refluxing time of 9 h the reaction mixture was mixed with 100 ml of water. The methyl ethyl ketone layer is separated, shaken twice with a 20% by weight sodium chloride solution and dried with sodium sulphate. The residue left after evaporation of the solvent was stirred with methanol, whereupon the precipitate formed was filtered with suction and recrystallized from methanol.

Yield: 12.5 g. Melting point: 44°–47° C.

Step 3

2-methyl-6-allyl-5-hexadecanoylhydroquinone 12 g of allyl ether of step 2 were subjected to the Claisen rearrangement as described for compound 17, step 3. The product formed was purified with benzine (boiling range: 50°–75° C.)

Yield: 8.5 g. Melting point: 65°–67° C.

Step 4:

2-methyl-6-propyl-5-hexadecanoylhydroquinone 8 g of allylhydroquinone of step 3 were hydrogenated as described for compound 17, step 4. The product formed was likewise recrystallized from benzine.

Yield: 6.5 g. Melting point: 66°–68° C.

Step 5:

2-methyl-6-propyl-5-$\alpha$-hydroxyhexadecylhydroquinone 6.5 g of the keto-compound of step 4 were dissolved in 90 ml of methanol and hydrogenated with a solution of 0.75 g of sodium borohydride in 8 ml of water as described for compound 17, step 5. The crude carbinol formed was recrystallized from methanol.

Yield: 5 g. Melting point: 121°–124° C.

Step 6:

Dye sulphinic acid 4-(3-[8-(4-nitro-2-methylsulphonylphenylazo)-5-hydroxynaphthyl]-sulphamylbenzene)-sulphonamidobenzenesulphinic acid 10 g of 3-[8-(4-nitro-2-methylsulphonylphenylazo)-5-hydroxynaphthyl]-sulphamylbenzene sulphonylchloride were introduced with stirring into a solution of 4.9 g of potassium carbonate, 3.75 g of p-aminobenzene sulphinic acid, 44 ml of water and 62.5 ml of acetone within 20 min. After 30 min the mixture was filtered and 250 ml of water and 31 ml of strong hydrochloric acid were added successively to the solution. The precipitate formed was filtered with suction, washed with water and dried in the drying stove.

Step 7

Compound No. 27

Under nitrogen atmosphere a filtered and 85° C. hot solution of 8.9 g of dye sulphinic acid, 1 g of anhydrous sodium acetate in 200 ml of glacial acetic acid and 120 ml of water was added with stirring at 60°–65° C. to a solution of 4.1 g of carbinol of step 5 in 250 ml of glacial acetic acid and stirred at 60°–65° C. for 1 h. After cooling the precipitate formed was filtered with suction and recrystallized from an ethyl acetate/methanol mixture in the presence of active carbon.

Yield: 5.5 g.

Preparation of compound No. 37

(a) 1-phenyl-3-methyl-4-(2-methoxy-5-chlorosulphonylphenylazo)-pyrazolone-(5).

826 g of the sodium salt of 1-phenyl-3-methyl-4-(2-methoxy-5-sulphonic acid phenylazo)-pyrazolone-(5) were stirred in 6 l of toluene, whereupon as much of a mixture of toluene and water was distilled that the condensate became clear. Then fresh toluene was added so as to restore the original volume, whereupon the solution was allowed to cool to 70° C. Then 80 ml of dimethylformamide were added and thereafter 580 ml of thionyl chloride were added at 70° C. in 30 min. The mixture was stirred at 80° C. for another 30 min and the end of the reaction was established by thin-layer chromatography. The excess thionyl chloride was evaporated at 90° C. whereupon the reaction was finished under slightly reduced pressure. The reaction mixture was allowed to cool to 25° C. and the precipitate formed was filtered with suction and washed with 1 l of toluene. It was dried first at 30° C. in a ventilated oven and then in a vacuum oven.

Yield: 882 g.

Every mole of the product contains 1 mole of sodium chloride. By thin-layer chromatography with methylene chloride/methanol mixture (98/2) as an eluent a faint side-spot of dye sulphonic acid was detected.

(b) 4-[4-(1-phenyl-3-methyl-pyrazolone-(5)-(3)-azo)4-methoxybenzenesulphonamido]-benzenesulphinic acid potassium salt 116.5 g of intermediate product (a) and 43.1 g of p-aminobenzenesulphinic acid together with 69 g of anhydrous potassium carbonate were refluxed for 2 h in a mixture of 700 ml of acetonitrile and 70 ml of water. After cooling and filtering 200 g of crude product consisting of about 60% of compound (c) were obtained.

(c) Compound No. 37.

17.5 g of 2,3-dimethyl-5-α-hydroxytetradecylhydroquinone prepared as described in Belgian Pat. No. 861,241, already mentioned hereinbefore, 44 g of intermediate compound (b) and a mixture of 200 ml of propionic acid and 25 ml of water were refluxed for 1 h. The reaction mixture was cooled till 60° C. and 100 ml of water were added. The precipitate formed was sucked off, washed with methanol and dried. Yield: 22.7 g. The product was purified by recrystallization from a mixture of 600 ml of acetonitrile and 60 ml of water.

Yield: 16.6 g. Melting point: 185° C.

(d) Preparation of the quinone compound corresponding with the hydroquinone compound 37

17.2 g of compound 37 were dissolved in 400 ml of ethanol at reflux temperature. To the solution 2.6 g of p-benzoquinone dissolved in 80 ml of ethanol were added. After 5 min reaction product started to precipitate. The boiling with reflux was continued for 15 min and thereupon the reaction mixture cooled to room temperature. The precipitate was sucked off, washed with ethanol and dried.

Yield: 16 g. Melting point: 140° C.

Preparation of compound No. 38

(a) 7-[1-methylsulphonylamino-4-(p-methylsulphonylphenylazo)]-naphthalene sulphonic acid.

Whilst stirring 188 g of p-methylsulphonylaniline were diazotized at 5° C. in a mixture of 3 l of water and 275 ml of 12 N hydrochloric acid whereto 81 g of sodium nitrite dissolved in 200 ml of water were added dropwise. After the addition the reaction mixture was stirred for still 30 min. The excess of nitrite was decomposed by adding urea.

Meanwhile 224 g of α-naphthylamine-7-sulphonic acid were dissolved in 2 l of pyridine at 30° C. 94 ml of methylsulphonylchloride were added and stirring continued for 30 min. To the obtained mixture the above diazonium salt solution was added dropwise keeping the temperature at 5° C. Stirring was continued for 1 h. Thereupon 2 l of 12 N hydrochloric acid were added and the reaction mixture left overnight. The precipitate was sucked off and washed three times with 500 ml of water containing 10% by weight of sodium chloride.

After drying 550 g of product (a) still containing 10% of sodium chloride were obtained.

Melting point: >260° C.

(b) 7-[1-methylsulphonylamino-4-(p-methylsulphonylphenylazo)]-naphthalene sulphonyl chloride.

510 g of intermediate product (a) were put whilst stirring at 60° C. into a mixture of 1250 ml of dichloroethane and 106 ml of N-methylpyrrolidone.

318 ml of phosphorus oxytrichloride were added dropwise. The obtained reaction mixture was stirred for 2 h at 70° C. and thereupon cooled till 5° C. The precipitate was sucked off and washed with methylene chloride and dried. The precipitate was stirred in 3 l of water and again sucked off, washed and dried.

Yield: 250 g. Melting point: >260° C.

(c) 4-[(1-methylsulphonylamino)-(4-p-methylsulphonylphenylazo)-naphthalene-(7)-sulphamido]-benzene sulphinic acid.

In 200 ml of water 30.3 g of anhydrous potassium carbonate and 18.8 g of p-aminobenzene sulphinic acid were dissolved. To this solution 350 ml of acetone were added and further portionwise whilst stirring 50.2 g of intermediate product (b). After the addition the reaction mixture was kept stirring for 1 h and thereupon poured into 1 l of water. To the aqueous solution portions of 50 ml of 12 N hydrochloric acid were added whereby a resinous precipitate was obtained. The supernatant aqueous layer was decanted and the resinous product treated with fresh water till a grainy solid structure was obtained. The grainy solid was separated by filtering with suction and dried.

Yield of crude procut: 43 g.

The product was purified by dissolving in a mixture 250 ml of aceton and 50 ml of ammonia (containing 25% of water) thereupon adding 900 ml of ethyl acetate.

The solvent phase was discarded and the oily residue stirred into 220 ml of 12 N hydrochloric acid till a solid product was obtained. The solid was separated by filtering, washed with a little ethanol and dried.

Yield: 23.3 g.

(d) Compound 38

12.3 g of intermediate product (c) and 7.2 g of 2,3-dimethyl-5-$\alpha$-hydroxytetradecyl-hydroquinone were refluxed for 2 h in 160 ml of acetic acid. Thereupon the reaction mixture was cooled to room temperature and filtered. The filtrate was poured into 400 ml of water, the precipitate separated by suction filtering, washed with water and dried. Yield: 11 g.

(e) Preparation of the quinone compound corresponding with the hydroquinone compound 38

11 g of compound 38 were dissolved in 140 ml of ethanol at reflux temperature. To the solution 1.5 g of p-benzoquinone dissolved in 30 ml of ethanol were added. The reaction mixture was boiled with reflux for 15 min. Thereupon the solvent was evaporated and the brown resinous product purified by column-chromatography using as eluent a mixture of methylene chloride and methanol 98/2.

Yield: 1.5 g.

Preparation of compound 39

(a) 1-hydroxy-3-(2-methylsulphonyl-4-nitrophenylazo)-4-(3-sulphonic acid sodium salt benzene sulphonamido)naphthalene.

70.5 g of the sulphonyl fluoride compound described in U.S. Pat. No. 3,942,987 of Richard A. Landholm, Jan R. Haase and James J. Krutak, Sr., issued Mar. 9, 1976, as compound A in column 32 are heated at 50° C. for 30 min with 14 g of sodium hydroxide dissolved in 1150 ml of water. In the reaction mixture 230 g of sodium chloride were dissolved. The reaction mixture was acidified with 46 ml of 12 N hydrochloric acid, 30 min stirred and the solid product obtained separated by suction filtering. Yield: 97 g. The product still contains 25% by weight of sodium chloride.

(b) 1-hydroxy-3-(2-methylsulphonyl-4-nitrophenylazo)-4-(3-chlorosulphonyl benzene sulphonamido)naphthalene.

98.5 g of intermediate product (a) are heated to 60° C. with 510 ml of phosphorus oxytrichloride. To the reaction mixture 15 ml of N-methylpyrrolidone were added dropwise. The reaction mixture was kept at 60° C. for 6 h whilst stirring. Thereupon the reaction mixture was cooled down and left overnight. The crystals formed were separated by suction filtering and dried.

The crystals were stirred in water, sucked off again, washed with water and dried. Yield: 108 g.

(c) 1-hydroxy-3-(2-methylsulphonyl-4-nitrophenylazo)-4-[3-(p-sulphobenzene aminosulphonyl)benzene sulphonamido]naphthalene.

17.3 g of p-aminobenzene sulphinic acid and 30.1 g of anhydrous potassium carbonate were dissolved in a mixture of 250 ml of water and 400 ml of acetone. Thereupon 62.4 g of intermediate product (b) were added thereto at once. The reaction mixture was stirred for 2 h at room temperature and poured into 1 l of water whereto 150 ml of 12 N hydrochloric acid were added. The precipitate was sucked off, washed first with water and then with methanol.

Yield: 67.5 g of crude product.

The purification proceeded by stirring it in 700 ml of water wherein 20 g of sodium hydrogenium carbonate were dissolved. The precipitate was separated by suction filtering, washed with a little water and dried.

Yield: 52 g.

(d) Compound 39.

14.9 g of intermediate product (c) and 7.7 g of 2,3-dimethyl-5-$\alpha$-hydroxytetradecyl-hydroquinone prepared as described in Belgian Pat. No. 861,241, already mentioned hereinbefore, were dissolved in 180 ml of acetic acid and refluxed for 1 h. To the cooled reaction mixture 500 ml of ethyl acetate and 400 ml of water were added and vigorously shaked. The ethyl acetate phase was washed once with 400 ml of water and then washed four times with 300 ml of a 10% by weight aqueous solution of sodium acetate.

The separated ethyl acetate phase was dried with anhydrous sodium sulphate and thereupon after removal of the sodium sulphate the solvent was evaporated.

Yield of crude product: 13.2 g.

The product was purified by column chromatography.

Yield: 3.9 g.

(e) Preparation of the quinone compound corresponding with the hydroquinone compound 39.

3.9 g of compound 39 and 0.5 g of p-benzoquinone were dissolved in 80 ml of ethanol and boiled with reflux for 1 h. The reaction mixture was cooled, the precipitate sucked off, washed with ethanol and dried.

Yield: 3.3 g. Melting point: 193° C.

Preparation of compound 40

(a) 1,4-methano-1,2,3,4-tetrahydro-6-tridecylcarbonyl-5,8-naphthoquinone.

89 g of myristic acid were melted at an oil-bath of 80° C. and to the melt 45.8 g of 1,4-methano-1,2,3,4-tetrahydro-5,8-naphthoquinone prepared as described in the U.S. Pat. No. 3,980,479, already mentioned hereinbefore, were added. Into the obtained mixture boron trifluoride gas was introduced till 45 g thereof were accepted. Then the reaction mixture was heated to 120° C. and kept at that temperature for 2 h. The reaction mixture was poured into a 5% by weight aqueous sodium carbonate solution. The formed precipitate was sucked off and purified by column chromatography. Yield: 73 g.

After recrystallization from benzine 56 g of product (a) melting at 60° C. were obtained.

(b) 1,4-methano-1,2,3,4-tetrahydro-6-$\alpha$-hydroxy-tetradecyl-5,8-naphthoquinone.

85 L g of intermediate product (c) were dissolved in 9 ml of ethanol containing Raney nickel as a catalyst. The reduction with hydrogen gas was carried out under a pressure of $8.27 \times 10^6$ Pa at 60° C. The Raney-nickel was filtered off and the filtrate poured into ice water. A viscous oily precipitate was obtained, which was treated with fresh water till a grainy solid was obtained. The precipitate was separated by suction filtering and dried.

Yield: 79 g. Melting point: 94° C.

The product was recrystallized from 800 ml of benzine.

Yield: 51 g. Melting point: 95° C.

(c) Compound 40.

1,4-methano-1,2,3,4-tetrahydro-6-α-hydroxy-tetradecyl-5,8-naphthoquinone.

10.6 g of intermediate product (b) used in the preparation of compound 37 were dissolved by boiling with reflux in a mixture of 80 ml of propionic acid and 10 ml of water. 7.8 g of the above intermediate carbinol compound (b) dissolved in 25 ml of ethylene glycol monomethyl ether were added dropwise in a period of 45 min to the refluxing solution. Thereupon the reaction mixture was cooled and poured with stirring into 500 ml of ice water whereto 15 ml of 12 N hydrochloric acid were added. After 2 h the precipitated product in the form of a yellow viscous oil is stirred with fresh water till solidification. The product is separated by suction filtering and dried.

Yield: 12 g. Melting point: 210° C. (unsharp).

(d) Preparation of the quinone compound corresponding with the hydroquine compound 40.

12 g of compound 40 were dissolved in 250 ml of ethanol and 3.2 g of p-benzoquinone added. The reaction mixture was boiled with reflux for 1 h. Thereupon the reaction mixture was cooled, the precipitate separated by suction filtering, washed with ethanol and dried.

Yield: 3.7 g. Melting point: 161° C.

We claim:

1. A photographic silver halide material comprising a support carrying at least one unexposed alkali-permeable silver halide hydrophilic colloid emulsion layer which contains in operative contact therewith or therein a quinone-type compound that is immobile in an alkali-permeable colloid medium and that contains a photographically useful group and a ballast group, wherein said compound is capable of being reduced by a silver halide developing agent at a rate slower than that of imagewise developable silver halide in the photographic material and in reduced state is capable of releasing said photographically useful group under alkaline conditions, characterized in that said quinone-type compound corresponds to one of the following formulae (A) or (B):

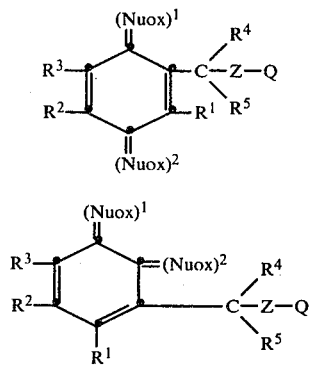

wherein:
each of $(Nuox)^1$ and $(Nuox)^2$ (same or different) represents an oxidized nucleophilic group, Z represents a bivalent atomic group which is electronegative with respect to the carbon atom carrying $R^4$ and $R^5$, Q together with the Z group represents a releasable photographically useful group, each of $R^1$, $R^2$ and $R^3$ is hydrogen, halogen, alkyl, alkoxy, or an acylamino group or $R^1$ and $R^2$ when in adjacent positions on the ring together form a ring fused with the remainder of the molecule, or $R^2$ and $R^3$ together form a ring fused with the remainder of the molecule, each of $R^4$ and $R^5$ (same or different) represents hydrogen or a hydrocarbon group, and in at least one of the substituents $R^1$, $R^2$, $R^3$, $R^4$ or $R^5$ a ballasting group X of sufficient size is present to render said compound immobile in an alkali-permeable layer of the photographic material.

2. A photographic material according to claim 1, characterized in that the photographically useful group Q after release represents a dye.

3. A photographic material according to claim 1, characterized in that the group $(Nuox)^1$ and the group $(Nuox)^2$ each are O= groups stemming from the oxidation of HO-groups.

4. A photographic material according to claim 1, characterized in that Z represents a sulphonyl group.

5. A photographic material according to claim 1, comprising a support carrying (1) a red-sensitive silver halide emulsion layer having operatively associated therewith a said quinone type compound that is initially immobile in an alkali-permeable colloid medium and wherefrom through the reducing action of a silver halide developing agent and alkalinity a cyan dye is split off in diffusible state, (2) a green-sensitive silver halide emulsion layer having operatively associated therewith said compound of (1) with the difference that a magenta dye is split off in diffusible state, and (3) a blue-sensitive silver halide emulsion layer having operatively associated therewith said compound of (1) with the difference that a yellow dye is split off in diffusible state.

6. A photographic material according to claim 5, wherein the photographically useful group is a shifted dye.

7. A photographic material according to claim 1, wherein the silver halide emulsion layer(s) is (are) negative working.

8. A photographic material according to claim 1, wherein the photosensitive silver halide emulsion layer(s) is (are) negative-working and applied to the same support as a receptor layer so as to form an integral combination of light-sensitive layer(s) with a non light-sensitive layer receiver element and an opaque layer, which is alkali-permeable, reflective to light and located between the receptor layer and the silver halide emulsion layer(s).

9. A photographic material according to claim 1, characterized in that the material is a film unit that is adapted to be processed by passing said unit between a pair of juxtaposed pressure-applying members, said unit comprising (1) a photosensitive element, which contains a silver halide emulsion layer having associated therewith said quinone type compound that is initially immobile in an alkali-permeable colloid medium and wherefrom through the reducing action of a silver halide developing agent and alkalinity a dye is split off in diffusible state, (2) an image dye-receiving layer, (3) means for discharging an alkaline processing composition within the film unit, said means being a rupturable container, which is adapted to be positioned during processing of the film so that a compressive force applied to the container by the pressureapplying members will effect a discharge of the container's contents within the film, and (4) a silver halide developing agent, which is soluble in an alkaline processing composition located within said film unit.

10. A photographic material according to claim 1, characterized in that the silver halide emulsion layer(s) contain(s) a silver halide developing agent.

11. A process for the production of diffusion transfer images, said process being characterized by the steps of (1) applying an alkaline processing composition to an image-wise exposed photographic material comprising a support carrying at least one silver halide emulsion layer and at least one alkali-permeable layer (which may be the same layer as the one containing the silver halide) which comprises a quinone type compound as defined hereinafter and that is initially immobile in an alkali-permeable colloid medium, wherein said compound is capable of being reduced by a silver halide developing agent at a rate slower than that of image-wise developable silver halide in the material and in reduced state is capable under alkaline conditions of releasing said photographically useful group, (2) providing said developing agent for said photographic material during application of said alkaline processing composition under conditions to effect image-wise release of said photographically useful group inversely proportionally to the image-wise development of said silver halide in the photographic material, and (3) allowing the diffusion with said alkaline processing composition of the photographically useful group out of the layer in which it was originally incorporated to have it introduced image-wise in another layer, said quinone-type compound corresponding to one of the following formula (A) or (B):

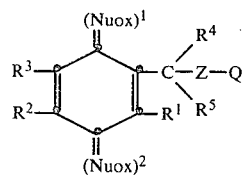
(A)

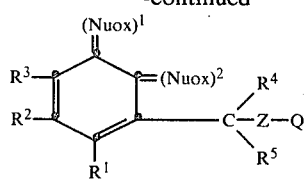
(B)

wherein:
each of $(Nuox)^1$ and $(Nuox)^2$ (same or different) represents an oxidized nucleophilic group,
Z represents a bivalent atomic group which is electronegative with respect to the carbon atom carrying $R^4$ and $R^5$,
Q together with the Z group represents a releasable photographically useful group,
each of $R^1$, $R^2$ and $R^3$ is hydrogen, halogen, alkyl, alkoxy, or an acylamino group or $R^1$ and $R^2$ when in adjacent positions on the ring together form a ring fused with the remainder of the molecule, or $R^2$ and $R^3$ together form a ring fused with the remainder of the molecule,
each of $R^4$ and $R^5$ (same or different) represents hydrogen or a hydrocarbon group, and in at least one of the substituents $R^1$, $R^2$, $R^3$, $R^4$ or $R^5$ a ballasting group X of sufficient size is present to render said compound immobile in an alkali-permeable layer of the photographic material.

12. A process according to claim 11, characterized in that said process is a photographic colour diffusion transfer process comprising the steps of:
(a) treating the photographic material with an alkaline processing composition in the presence of a silver halide developing agent to effect development of the exposed silver halide emulsion layer(s), thereby image-wise oxidizing the developing agent and as an inverse function of image-wise silver halide development reducing said immobile compound(s) that in reduced state are capable of releasing (a) dye(s);
(b) maintaining said photographic material in the alkaline medium of the processing composition for a time sufficient to release said dye(s) in diffusible state from the reduced immobile compound(s); and
(c) transferring at least a portion of said dye(s) to a non-light-sensitive layer acting as a receptor layer.

* * * * *